US00PP33470P2

(12) United States Plant Patent
Hartman

(10) Patent No.: US PP33,470 P2
(45) Date of Patent: Sep. 7, 2021

(54) ***CALADIUM* PLANT NAMED 'GPR SWT STR 013-993'**

(50) Latin Name: ***Caladium* X *hortulanum***
Varietal Denomination: GPR SWT STR 013-993

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/013,785

(22) Filed: Sep. 7, 2020

(51) Int. Cl.
*A01H 5/00* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — C. Anne Whealy

(57) ABSTRACT

A new and distinct cultivar of *Caladium* plant named 'GPR SWT STR 013-993', characterized by its intermediate height; somewhat mounding plant habit; dense and bushy appearance; vigorous growth habit and rapid growth rate; thick and rigid lance-type leaves that are purplish red or white predominantly and variably flushed with purplish red with dark purplish grey-colored venation and dark green-colored margins; petioles that are black or brownish green in color with black-colored stippling, stripes and streaks; and excellent garden performance with tolerance to full sunlight, wind and rain.

7 Drawing Sheets

Figure 1:
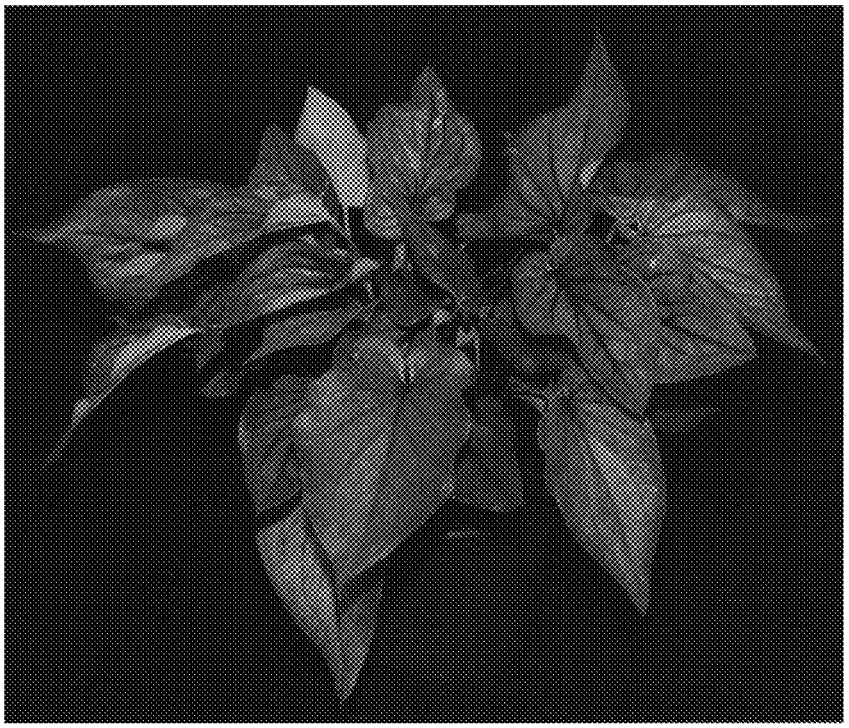

Botanical designation: *Caladium* X *hortulanum*.
Cultivar denomination: 'GPR SWT STR 013-993'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'GPR SWT STR 013-993'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'Florida Sweetheart', disclosed in U.S. Plant Pat. No. 8,526, as the female, or seed, parent with an unnamed proprietary selection of *Caladium* X *hortulanum* primarily used as a breeding parent, not patented, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'GPR SWT STR 013-993'. These characteristics in combination distinguish 'GPR SWT STR 013-993' as a new and distinct *Caladium* plant:

1. Intermediate in height and somewhat mounding plant habit; dense and bushy appearance.
2. Vigorous growth habit and rapid growth rate.
3. Thick and rigid lance-type leaves that are purplish red or white predominantly and variably flushed with purplish red with dark purplish grey-colored venation and dark green-colored margins.
4. Petioles that are black or brownish green in color with black-colored stippling, stripes and streaks.
5. Excellent garden performance with tolerance to full sunlight, wind and rain.

Plants of the new *Caladium* differ primarily from plants of the female parent, 'Florida Sweetheart', in the following characteristics:

1. Plants of the new *Caladium* are taller and more upright than plants of 'Florida Sweetheart'.
2. Plants of the new *Caladium* and 'Florida Sweetheart' differ in leaf color as leaves of the new *Caladium* are purplish red or white predominantly flushed with purplish red with dark purplish grey-colored venation and dark green-colored margins whereas leaves of 'Florida Sweetheart' have dark pink-colored venation, rose pink-colored interveinal areas with greenish white-colored margins.
3. Plants of the new *Caladium* and 'Florida Sweetheart' differ in leaf petiole color as leaf petioles of the new *Caladium* are black or brownish green in color with black-colored stippling, stripes and streaks in color whereas leaf petioles of 'Florida Sweetheart' are tannish pink in color with darker-colored stripes.

Plants of the new *Caladium* differ primarily from plants of the male parent selection in the following characteristics:

1. Leaves of plants of the new *Caladium* are thicker and more undulate than leaves of plants of the male parent selection.
2. Plants of the new *Caladium* and the male parent selection differ in leaf color as leaves of the new *Caladium* are purplish red or white predominantly flushed with purplish red with dark purplish grey-colored venation and dark green-colored margins whereas leaves of the male parent selection are white to greenish white in color flushed with reddish purple.

Plants of the new *Caladium* can be compared to plants of *Caladium* X *hortulanum* 'Green Pearl', not patented. In side-by-side comparisons, plants of the new *Caladium* differ primarily from plants of 'Green Pearl' in the following characteristics:

1. Plants of the new *Caladium* grow faster than plants of 'Green Pearl'.
2. Plants of the new *Caladium* and 'Green Pearl' differ in leaf color as leaves of the new *Caladium* are purplish red or white predominantly flushed with purplish red with dark purplish grey-colored venation and dark green-colored margins whereas leaves of 'Green Pearl' are predominately white or greenish white in color with green to dark green-colored venation and thin green-colored margins.
3. Plants of the new *Caladium* and 'Green Pearl' in leaf petiole color as leaf petioles of the new *Caladium* are black or brownish green in color with black-colored stippling, stripes and streaks in color whereas leaf petioles of 'Green Pearl' are green to tannish green in color.

Plants of the new *Caladium* can also be compared to plants of *Caladium* X *hortulanum* 'Blushing Bride', disclosed in U.S. Plant Pat. No. 22,213. In side-by-side comparisons, plants of the new *Caladium* differ primarily from plants of 'Blushing Bride' in the following characteristics:

1. Plants of the new *Caladium* and 'Blushing Bride' differ in leaf color as leaves of the new *Caladium* are purplish red or white predominantly flushed with purplish red with dark purplish grey-colored venation and dark green-colored margins whereas leaves of 'Blushing Bride' are greyed purple in color with dark green-colored margins and whitish-colored venation tinged with greyed purple.
2. Plants of the new *Caladium* and 'Blushing Bride' in leaf petiole color as leaf petioles of the new *Caladium* are black or brownish green in color with black-colored stippling, stripes and streaks in color whereas leaf petioles of 'Blushing Bride' are tannish pink to tannish green in color with dark brownish green-colored stippling, streaks and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'GPR SWT STR 013-993' in a container and grown in a shade house (tuber de-eyed).

Figure 2:
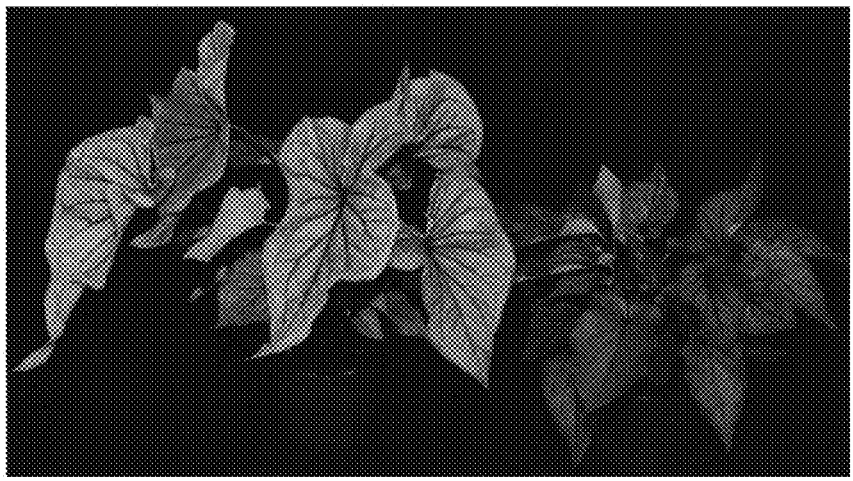
Figure 3:
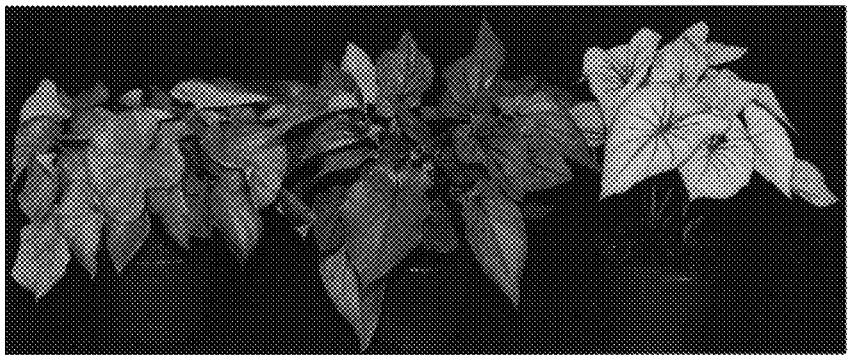

The photograph on the second sheet (FIG. 2) is a comparison view of typical plants of 'GPR SWT STR 013-993' grown in containers, the plant on the left has not had its tuber de-eyed and the plant on the right has had its tuber de-eyed prior to planting; the photograph on the third sheet (FIG. 3) is side perspective view of the female parent, 'Florida Sweetheart' (left), 'GPR SWT STR 013-993' (center) and the male parent selection (right).

Figure 4:
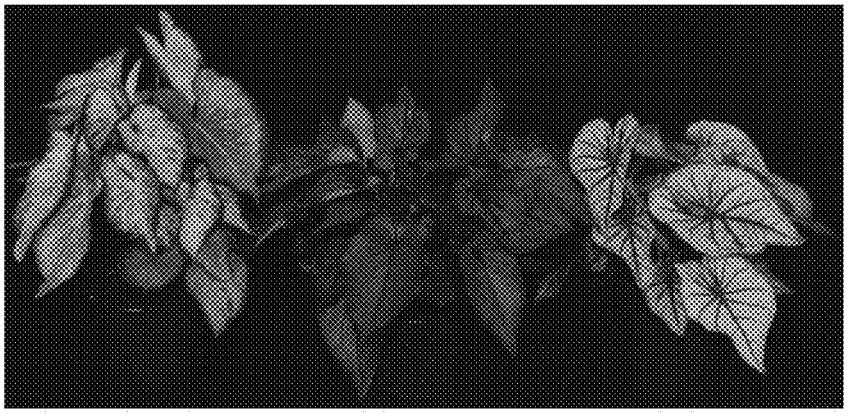

The photograph on the fourth sheet (FIG. 4) is a comparison view of typical potted plants of 'Blushing Bride' (left), 'GPR SWT STR 013-993' (center) and 'Green Pearl' (right).

Figure 5:
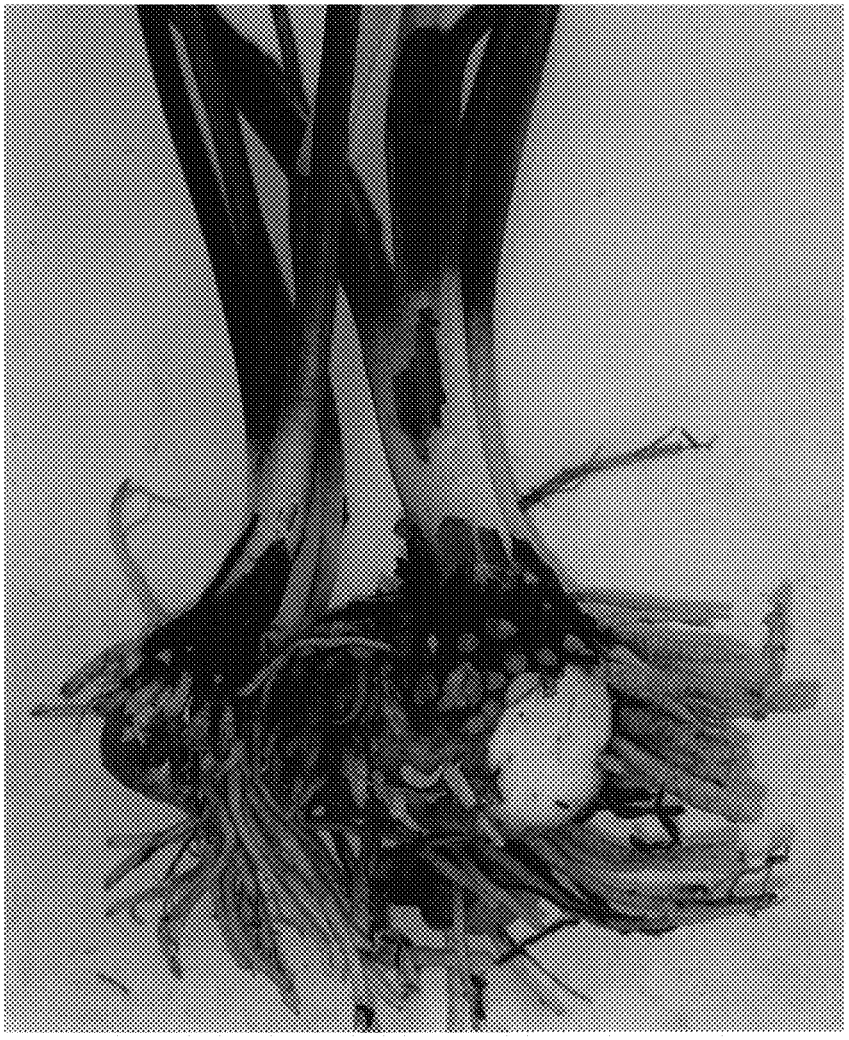

The photograph on the fifth sheet (FIG. 5) is a close-up view of typical freshly-harvested tubers with roots and leaf petioles of 'GPR SWT STR 013-993'.

Figure 6:
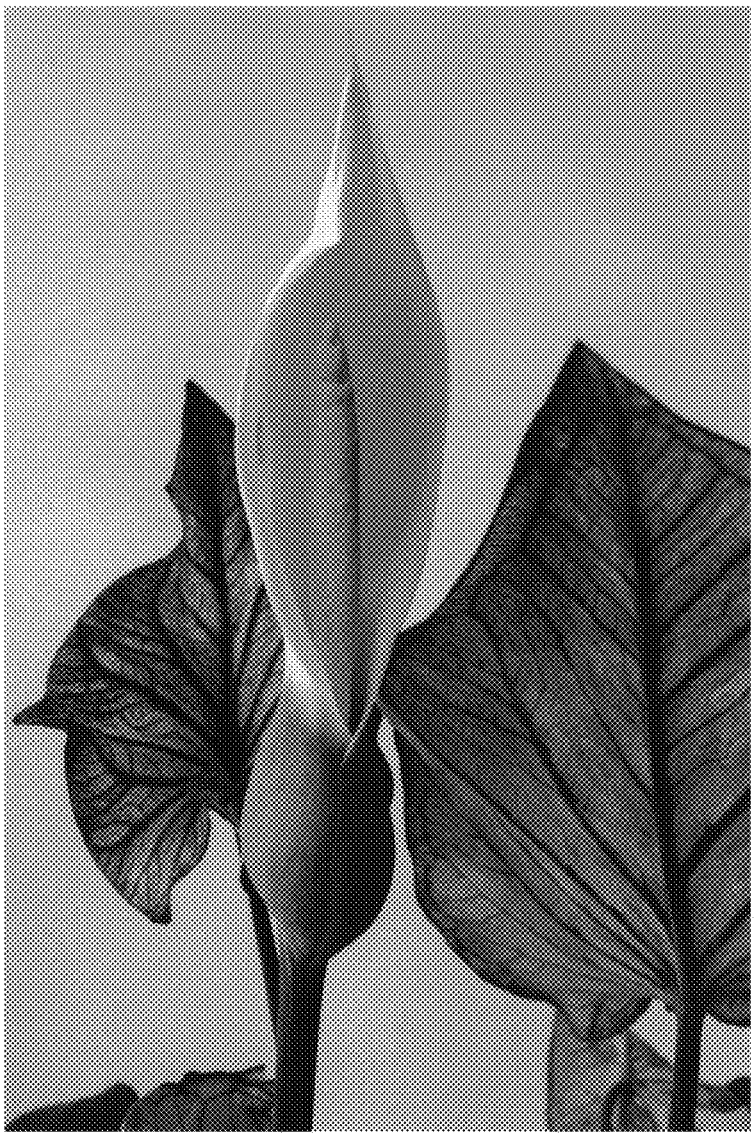

The photograph on the sixth sheet (FIG. 6) is a close-up view of a typical inflorescence of 'GPR SWT STR 013-993'.

Figure 7:
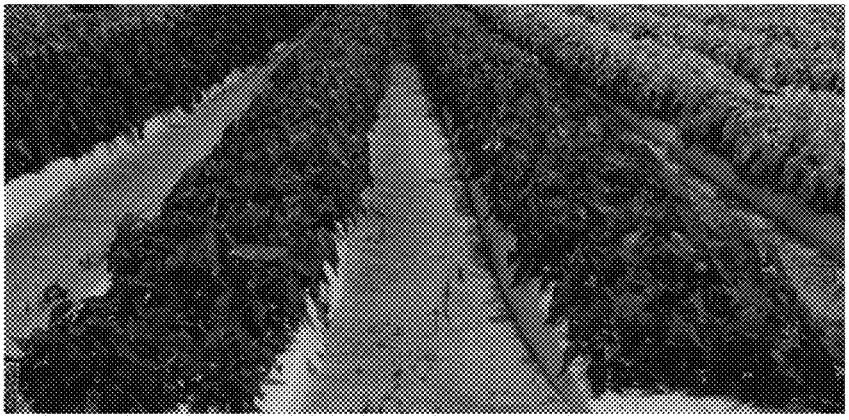

The photograph on the seventh sheet (FIG. 7) is a side perspective view of typical plants of 'GPR SWT STR 013-993' grown in an open production field.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were six weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'GPR SWT STR 013-993'.

Parentage:

*Female, or seed, parent.*—*Caladium* X *hortulanum* 'Florida Sweetheart', disclosed in U.S. Plant Pat. No. 8,526.

*Male, or pollen, parent.*—Unnamed proprietary selection of *Caladium* X *hortulanum* primarily used as a breeding parent, not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments mostly elliptic in shape. Height: About 2.8 cm. Diameter: About 5.1 cm to 6.2 cm. Segment height: About 2.3 cm. Segment diameter: About 1.8 cm. Axillary bud shape: Roughly triangular. Axillary bud size: About 4 mm by 4 mm. Texture: Thick, starchy; somewhat brittle. Color: Periderm, freshly-harvested: Close to 199B. Periderm, dried: Close to 200A to 200B. Epidermis: Initially, close to 179D becoming closer to 38D with development. Cortical tissue: Close to NN155C and 1D. Axillary buds: Close to 38B. Root description: Thick, fleshy contractile roots with few lateral branches; color, close to NN155D. Rooting habit: Medium density.

Plant description:

*Plant type.*—Herbaceous perennial; suitable as a potted plant in containers 15-cm to 25-cm and suitable as a landscape plant in shaded areas.

*Plant and growth habit.*—Intermediate in height, upright and somewhat mounding plant habit; dense and bushy appearance; vigorous growth habit and rapid growth rate; potted plants finish in saleable form in about six weeks after planting tubers; leaf petioles and leaves arise from one or more growing points on tubers; leaf petioles initially upright and leaning and arching outwardly with development.

*Plant height, from soil level to top of foliar plane, shade house-grown potted plants, tubers de-eyed.*—About 22 cm to 24 cm.

*Plant height, from soil level to top of foliar plane, shade house-grown potted plants, tubers not de-eyed.*—About 40 cm to 42 cm.

*Plant height, from soil level to top of floral plane, shade house-grown potted plants, tubers not de-eyed.*—About 54.5 cm.

*Plant diameter or spread, shade house-grown potted plants, tubers de-eyed.*—About 34 cm to 49 cm.

*Plant diameter or spread, shade house-grown potted plants, tubers not de-eyed.*—About 66 cm to 73 cm.

*Number of shoots per plant, shade house-grown potted plants, tubers de-eyed.*—About 11 to 14 develop per #1 tuber.

*Number of shoots per plant, shade house-grown potted plants, tubers not de-eyed.*—About three to four develop per #1 tuber.

*Cataphylls, shade house-grown potted plants.*—Length: About 4 cm to 4.5 cm. Width: About 1.2 cm to 1.7 cm. Shape: Linear to narrowly elliptic. Apex: Obtuse to emarginate. Base: Sheathing the stein. Color: Outer surface: Close to N155B densely streaked and stippled with close to 200A; color becoming closer to 200A stained with close to 187A with development. Inner surface: Close to N155A and N155C; colors and patterns on outer surface visible on inner surface.

Leaf description:

*Arrangement and type.*—Alternate; simple; lance-type.

*Length, shade house-grown potted plants.*—About 15 cm to 16.5 cm.

*Width, shade house-grown potted plants.*—About 8.5 cm to 11 cm; when flattened, about 10 cm to 12 cm.

*Shape.*—Ovate.

*Apex.*—Acute to acuminate.

*Base.*—Sagittate-peltate, cordate; basal leaf lobes may be imbricate.

*Margin.*—Entire; wavy with broad undulations.

*Texture and luster, upper surface.*—Smooth, glabrous; relatively thick; puckering between veins; slightly carinate; slightly glaucous; dull sheen.

*Texture and luster, lower surface.*—Smooth, glabrous; glaucous; dull sheen.

*Venation pattern.*—Pinnate and palmate.

*Color, shade house-grown potted plants.*—Fully developed leaves, upper surface: Background color: Close to 184C or close to NN155B predominantly and variably flushed with close to 184C and 187C; random flecks, close to 192C. Margins: Close to 147A or close to 147A flushed and flecked with close to N155C; at the leaf edge, close to 187A. Basal notch: Close to N186D. Midvein and primary venation: Close to N186A; areas surrounding venation, close to 146A or close to 146A tinged with close to 184C. Secondary venation: Close to 147B tinged with close to N186C or close to N186B. Fully developed leaves, lower surface: Background color: Close to N155C variably flushed with close to 183D. Margins: Close to 191B, 191C, and N155C tinged with close to 183D; at the leaf edge, close to 187A. Leaf attachment point: Close to 187A to 187B. Midvein and primary venation: Close to 177D and 182D variably streaked and blotched with close to 200A, 200B and 200C. Secondary venation: Close to 139A flushed with close to 200A, 200B and 200C.

*Petioles.*—Aspect: Initially upright and straight and leaning and arching outwardly with development; flexible. Length, shade house-grown potted plants, tubers de-eyed: About 16.5 cm to 21.5 cm. Length, shade house-grown potted plants, tubers not de-eyed: About 16 cm to 36 cm. Diameter, distally, shade house-grown potted plants, tubers de-eyed: About 3 mm to 4 mm. Diameter, distally, shade house-grown potted plants, tubers not de-eyed: About 5.5 mm to 6 mm. Diameter, proximally, shade house-grown potted plants, tubers de-eyed: About 6 mm to 7 mm. Diameter, proximally, shade house-grown potted plants, tubers not de-eyed: About 1 cm to 1.2 cm. Texture and luster: Smooth, glabrous; glossy to shiny. Color, shade house-grown potted plants: When developing and fully developed: Close to 202A and N200A variably streaked with close to N170D or close to N170D and 159C tinged with close to 148D and stippled, streaked and striped with close to 200C tinged with close to 148D; just below the leaf junction, close to 202A streaked with close to 181C. Wing length, shade house-grown potted plants, tubers de-eyed: About 4.5 cm to 7.4 cm. Wing length, shade house-grown potted plants, tubers not de-eyed: About 9 cm to 12.5 cm. Wing diameter, shade house-grown potted plants, tubers de-eyed: About 7 mm. Wing diameter, shade house-grown potted plants, tubers not de-eyed: About 1 cm to 1.2 cm. Texture and luster, inner and outer surfaces: Smooth, glabrous; dull sheen. Wing color, shade house-grown potted plants: Outer surface: Close to 202A tinged with close to N189A with stippling and marbling, close to N155B; distally, occasionally marbled with close to 36D. Inner surface: Close to N155B; distally, marbled with close to N200A and 202A; colors and patterns on the outer surface are visible on the inner surface.

Inflorescence description: Inflorescences observed on eight week-old shade house-grown potted plants.

*Inflorescence arrangement*.—Upright hooded spathes surrounding a columnar spadix borne on an upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring and summer in central Florida; flowers develop about eight weeks after growth commences; inflorescences last about three days before fading; inflorescences persistent.

*Spathe*.—Length, overall: About 19 cm. Length, distal open portion: About 13.5 cm. Length, proximal closed portion: About 5.5 cm. Width, distal open portion: About 4.8 cm. Depth, distal open portion: About 2.7 cm. Width, at constriction: About 2 cm. Width, proximal closed portion: About 3.5 cm. Shape, open portion: Narrowly elliptic to slightly obovate. Apex: Acute to acuminate. Base: Acute. Margin: Entire; open portion, reflexed. Texture and luster, front surface: Smooth, glabrous; dull sheen. Texture and luster, rear surface: Smooth, glabrous; distally, dull sheen and proximally, glaucous. Color, front surface: Distal open portion: Close to 155C; with development, color becoming closer to 199B and 200C. Proximal closed portion: Close to 148D and flushed towards the base with close to 187A; color does not change with development. Color, rear surface: Distal open portion: Close to 145D; towards the center, close to 145C; towards the margins, close to 157B; color does not change with development. Proximal closed portion: Close to 147C and 147D with random areas of close to N200A; color does not change with development.

*Spadix*.—Length, overall: About 12 cm. Length, male flower zone: About 6.2 cm. Length, sterile zone: About 2.8 cm. Length, female flower zone: About 3 cm. Diameter, male flower zone: About 1.3 cm. Diameter, sterile flower zone: About 1 cm. Diameter, female flower zone: About 1.3 cm. Shape: Columnar, spindle-shaped. Apex: Acute to obtuse. Base: Obtuse. Aspect: Upright. Color, mature, male zone: Close to 155D. Color, mature, sterile zone: Close to 155D. Color, mature, female zone: Close to 159D and 158B. Male flowers: Quantity per spadix: About 170. Shape: Obovate. Height: About 3.5 mm. Diameter: About 3.5 mm. Pollen amount: Abundant. Pollen color: Close to 4C. Female flowers: Quantity per spadix: About 350. Shape: Obovate. Height: About 3.5 mm. Diameter: About 2 mm. Stigma color: Close to 159D. Ovary color: Close to 158B.

*Scape*.—Length: About 35.5 cm. Diameter: About 9 mm. Strength: Sturdy; flexible. Aspect: Mostly erect. Texture and luster: Smooth, glabrous; distally, glaucous and proximally, glossy. Color: Close to 202A and N200A occasionally streaked with close to N170D; just below spathe, glaucous and close to 202A and N200A streaked with close to N155C.

*Seeds and fruits*.—To date, seed and fruit development have not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Garden performance & temperature tolerance: Plants of the new *Caladium* have been observed to have excellent garden performance with tolerance to full sunlight, wind and rain and to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'GPR SWT STR 013-993' as illustrated and described.

* * * * *